(12) United States Patent
Boiten et al.

(10) Patent No.: US 9,993,356 B2
(45) Date of Patent: Jun. 12, 2018

(54) ORTHOPEDIC DEVICE

(71) Applicant: OTTO BOCK HEALTHCARE GMBH, Duderstadt (DE)

(72) Inventors: Herman Boiten, Gottingen (DE); Luder Mosler, Duderstadt (DE); Martin Pusch, Duderstadt (DE); Frederik Te Riele, Hengelo (NL); Joachim Michniewicz, Munich (DE); Lenka Harbach, Hannover (DE)

(73) Assignee: OTTO BOCK HEALTHCARE GMBH, Duderstadt (DE)

( * ) Notice: Subject to any disclaimer, the term of this patent is extended or adjusted under 35 U.S.C. 154(b) by 102 days.

(21) Appl. No.: 14/646,705

(22) PCT Filed: Nov. 26, 2013

(86) PCT No.: PCT/EP2013/003567
§ 371 (c)(1),
(2) Date: May 21, 2015

(87) PCT Pub. No.: WO2014/079588
PCT Pub. Date: May 30, 2014

(65) Prior Publication Data
US 2015/0305895 A1    Oct. 29, 2015

(30) Foreign Application Priority Data

Nov. 26, 2012  (DE) .......................... 10 2012 023 023

(51) Int. Cl.
*A61F 2/64* (2006.01)
*A61F 2/66* (2006.01)
(Continued)

(52) U.S. Cl.
CPC .................. *A61F 2/68* (2013.01); *A61F 2/60* (2013.01); *A61F 2/604* (2013.01); *A61F 2/64* (2013.01);
(Continued)

(58) Field of Classification Search
CPC ................... A61F 2002/5006; A61F 2002/745
(Continued)

(56) References Cited

U.S. PATENT DOCUMENTS 111,741 A * 2/1871 Hanger ..................... A61F 2/64
623/42
2,478,721 A * 8/1949 Stewart .................. A61F 2/604
623/26

(Continued)

FOREIGN PATENT DOCUMENTS

CN    102316828 A    10/2012
CN    102724936 A    10/2012
(Continued)

OTHER PUBLICATIONS

Arnout, Matthys, et al., "Concept and Design of the HEKTA (Harvest Energy from the Knee and Transfer it to the Ankle) Transfemoral Prosthesis," submitted to Fourth IEEE RAS/EMBS International Conference on Biomedical Robotics and Biomechatronics, Received Jan. 31, 2012, 6 pages.

(Continued)

*Primary Examiner* — David H Willse
(74) *Attorney, Agent, or Firm* — Holland & Hart

(57) ABSTRACT

An orthopedic device for the orthotic or prosthetic provision of a patient. The orthopedic device includes a knee joint which has a proximal upper part and a distal lower part arranged pivotably thereon, an ankle joint, a pivoted foot part which can be fastened distally to the ankle joint, and a shin part arranged between the ankle joint and the knee joint.

(Continued)

The upper part of the knee joint or a thigh part fastened thereto that can be attached to the patient's body and is coupled with the foot part by means of a force transfer device, which causes a plantar flexion of the foot part when a knee is flexed.

19 Claims, 20 Drawing Sheets

(51) Int. Cl.
    *A61F 2/74*     (2006.01)
    *A61F 2/68*     (2006.01)
    *A61F 2/60*     (2006.01)
    *A61F 2/50*     (2006.01)
    *A61F 2/70*     (2006.01)
    *A61F 5/01*     (2006.01)
    *A61F 2/76*     (2006.01)

(52) U.S. Cl.
    CPC .............. *A61F 2/66* (2013.01); *A61F 2/6607* (2013.01); *A61F 5/0106* (2013.01); *A61F 5/0111* (2013.01); *A61F 2002/5003* (2013.01); *A61F 2002/5006* (2013.01); *A61F 2002/704* (2013.01); *A61F 2002/745* (2013.01); *A61F 2002/748* (2013.01); *A61F 2002/7625* (2013.01); *A61F 2005/0155* (2013.01)

(58) Field of Classification Search
    USPC ...................................................... 623/40–42
    See application file for complete search history.

(56) References Cited

U.S. PATENT DOCUMENTS

| | | | |
|---|---|---|---|
| 2,605,474 A * | 8/1952 | Oliver | ..................... A61F 2/604 623/26 |
| 4,370,761 A | 2/1983 | Serri | |
| 8,974,542 B2 | 3/2015 | Balboni et al. | |
| 9,278,013 B2 | 3/2016 | Seyr et al. | |
| 2004/0064195 A1 | 4/2004 | Herr | |
| 2006/0235544 A1 | 10/2006 | Iversen et al. | |
| 2006/0249315 A1 | 11/2006 | Herr et al. | |
| 2008/0269913 A1 | 10/2008 | Gobbers et al. | |
| 2009/0265018 A1 | 10/2009 | Goldfarb et al. | |
| 2009/0299489 A1 | 12/2009 | Gramnaes | |

FOREIGN PATENT DOCUMENTS

| | | |
|---|---|---|
| DE | 475303 B1 | 4/1929 |
| EP | 0041052 A1 | 12/1981 |
| FR | 2549719 A1 | 2/1985 |
| GB | 245577 | 1/1926 |
| RU | 2254832 C1 | 6/2005 |
| RU | 135255 U1 | 12/2013 |
| WO | 2011080556 A2 | 7/2011 |
| WO | 2012177125 A1 | 12/2012 |

OTHER PUBLICATIONS

Pillai, Minerva V., et al., "Design of a Semi-Active Knee-Ankle Prosthesis," 2011 IEEE International Conference on Robotics and Automation, May 9-13, 2011, Shanghai, China, pp. 5293-5300.

PCT International Search Report for PCT International Patent Application No. PCT/EP2013/003567, dated Mar. 27, 2014.

* cited by examiner

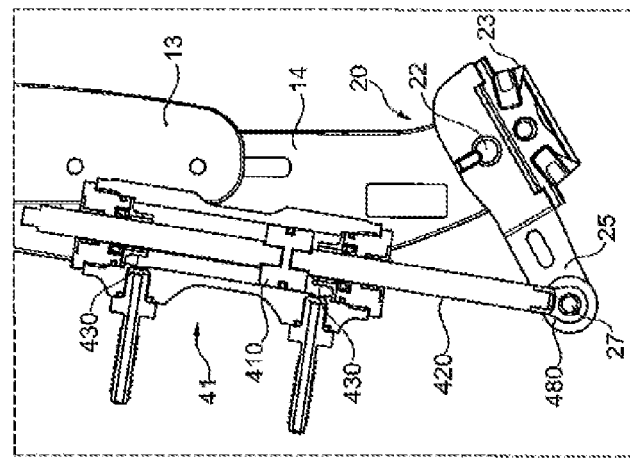
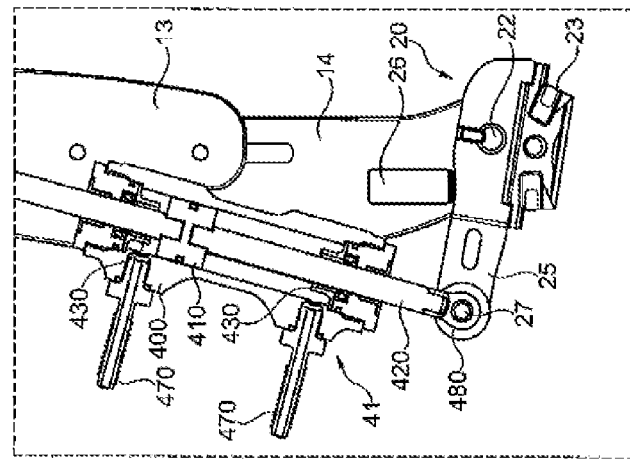

ORTHOPEDIC DEVICE

TECHNICAL FIELD

The invention relates to an orthopedic device for the orthotic or prosthetic provision of a patient, with a knee joint, which has a proximal upper part and a distal lower part arranged pivotably thereon about a knee axis, and an ankle joint with an ankle joint axis, a foot part which is arranged distally on the ankle joint and is pivotable about the ankle joint axis, and a shin part arranged between the ankle joint and the knee joint. The device can be fastened to the body of the patient via a thigh component arranged proximally on the knee joint.

BACKGROUND

The purpose of orthoses is to guide or support the movement of an existing limb or to brace and support the limb, while prostheses replace limbs that are not present. Leg orthoses are available in different embodiments, with those referred to as knee angle foot orthoses (KAFO) supporting both the foot and also the ankle joint and knee joint. The foot is generally placed on a foot plate, one or more shin rails extend parallel to the lower leg, a knee joint is provided approximately in the area of the knee axis, and fastening devices are mounted on one or more thigh rails in order to fasten the prosthesis to the upper leg. Likewise, fastening devices can be provided on the shin rails and on the foot plate so as to be able to fasten the orthosis on the respective leg.

Prosthetic devices with a prosthetic knee joint have a prosthetic foot, which is fastened to the prosthetic knee joint via a lower leg tube. Proximally from the prosthetic knee joint, a fastening device is provided for the prosthesis, which is usually designed as an upper leg socket into which the upper leg stump can be inserted. A prosthetic knee joint can have various designs ranging from a monoaxial prosthetic knee joint or a polycentric knee joint with damping means to computer-aided or driven active prosthetic knee joints. The prosthetic feet can be fastened to the lower leg tube either rigidly or in an articulated manner, while motor-driven prosthetic feet are also possible.

FR 2,549,719 A1 relates to a prosthesis with a prosthetic knee joint and with a prosthetic foot fastened to a lower leg tube in an articulated manner. A connection rod, which is coupled to the prosthetic knee joint via a lever mechanism, is arranged posterior to the ankle joint axis. When the prosthetic knee joint is flexed, the prosthetic foot is lifted and a dorsiflexion is performed.

US 2008/0269913 A1 relates to an artificial leg with a prosthetic knee joint and a prosthetic foot. On the prosthetic knee joint, a connection rod is articulated frontally with respect to the knee joint axis, such that, upon flexion of the knee, the connection rod is moved in a guide in the lower leg tube. The movement is conveyed to the prosthetic foot via a tensioning element, such that the tip of the foot is lifted in the knee flexion.

US 2009/0265018 A1 relates to a driven leg prosthesis and to a method for controlling the leg prosthesis in order to achieve an almost natural gait pattern. Both the prosthetic knee joint and also the ankle joint are provided with separate motor drives. The prosthesis is controlled in real time by sensors on the basis of different intramodal control programs.

EP 0 041 052 B1 relates to a prosthesis for a lower limb, in which an upper leg socket and a lower leg are coupled to each other via a toothed hinge. A spring-loaded piston rod lifts the toes in the event of a knee flexion.

DE 47 53 03 B1 relates to an artificial leg in which a lower leg part and an upper leg part are connected to each other by two articulated rods, in order to effect a dorsiflexion when the prosthetic knee joint is angled.

In prosthetic devices with a functional separation of knee joint and ankle joint, damping is often provided during the movement, such that the kinetic energy is converted to thermal energy. If there is a functional connection of knee joint and ankle joint, the kinetic energy is conveyed from the knee joint to the ankle joint.

SUMMARY

The object of the present invention is to make available a coupling between the knee joint and the ankle joint with the least possible outlay in terms of design, which coupling allows the kinetic energy of the knee to be used for the ankle movement, provides an approximation to the natural gait pattern and, at the end of the stance phase, minimizes a vertical movement of the center of gravity of the body.

According to the invention, this is achieved by an orthopedic device having the features of the main claim. Advantageous embodiments and developments of the invention are disclosed in the dependent claims, the description and the figures.

In the orthopedic device according to the invention for the orthotic or prosthetic provision of a patient, with a knee joint, which has a proximal upper part and a distal lower part arranged pivotably thereon, in particular about a fixed or instantaneous knee axis, and an ankle joint, which in particular has a fixed or instantaneous ankle joint axis, a pivotable foot part which is arranged distally on the ankle joint, and a shin part which is arranged between the ankle joint and the knee joint, provision is made that the upper part of the knee joint, or a thigh part that is fastened thereto, is coupled to a foot part via a force transmission mechanism, which causes a plantar flexion of the foot part when the knee is flexed. By coupling the upper part of the knee joint, or a thigh component which is arranged proximally on the knee joint and can be fastened to the patient's body, for example an upper leg rail or an upper leg socket, to a foot part via a force transmission mechanism which causes a plantar flexion of the foot part when the knee is flexed, it is possible to use the kinetic energy of the knee for the ankle movement. Analogously to the natural gait pattern, in which a plantar flexion is performed at the end of the stance phase in order to lengthen the length of the leg upon flexion of the knee, the foot part undergoes plantar flexion by way of the force transmission mechanism. In this way, the duration of the ground contact of the foot part is prolonged, as a result of which the vertical movement of the center of gravity of the body is minimized. By the energetic coupling of the knee flexion with the plantar flexion of the foot part, a high energy efficiency is achieved with low outlay in terms of equipment. When the knee joint is extended during the swing phase, a movement reversal can take place, such that a dorsiflexion of the foot part is brought about. Likewise, after a predetermined flexion angle is reached, the actuation of the prosthetic foot can be switched, such that, after the flexion angle is reached, a dorsiflexion is performed in order to reduce the effective leg length and, in the swing phase, particularly when bringing the foot forward, to prevent stumbling or catching on obstacles. A plantar flexion is understood as that movement in which a pivoting of the foot part in the direction of the ground takes place, such that the angle between the shin part and the foot part increases. Dorsiflexion is the opposite movement, in which the dorsum of the foot or the instep is moved in the direction of the tibia or the shin part and the angle between the dorsum or instep and the shin part decreases. The pivotable connection between the individual components can be realized via a single fixed shaft, i.e. an axle that allows only a rotation movement and is secured in a stable position on at least one of the components. Alternatively, in the case of polycentric joints, a displaceable instantaneous rotation axis can be realized which, on account of the polycentric bearing in multi-link joints, is not stationary relative to at least one component but instead migrates in the course of the pivoting movement. A virtual rotation axis arises about which the upper part pivots relative to the lower part or the shin part pivots relative to the foot part. It is also possible that the pivotable attachment of two components to each other is effected via an elastomer joint, such that no defined fixed rotation axis is present, and instead different rotation axes form within the elastomer joint under different loads, for example in the event of different transverse forces or torsional forces about an axis that extends in the proximal-distal direction.

The force transmission mechanism can be designed as a hydraulic system, such that a very compact and easy transmission of force from the knee joint to the foot part can take place via piston rods, hydraulic lines and valves. Likewise, the switch from plantar flexion to dorsiflexion can be performed very easily via a switch valve, which can be controlled mechanically or also electrically. Alternatively or in addition, a mechanical coupling mechanism can be provided that can be designed to transmit tensile force and/or compressive force. Mechanical coupling mechanisms have the advantage of a solid construction with a high degree of availability and easy repair possibilities. On account of the moved parts in a mechanical coupling, items of clothing or prosthetic linings may tear or become caught.

The mechanical coupling mechanism can be mounted on a first bearing point protruding dorsally or ventrally with respect to the knee axis and mounted on a second bearing point ventrally or dorsally with respect to the ankle joint axis, wherein the bearing points lie on different sides of a connection line between a knee axis and an ankle joint axis. In the case of a dorsally protruding first bearing point, the coupling mechanism is subjected to pressure during a flexion of the knee and transmits the forces at the end of the stance phase to the second bearing point lying ventrally with respect to the ankle joint axis, such that a moment arises about the ankle joint axis. In a reverse arrangement of the first bearing point, i.e. ventrally with respect to the knee axis, the moment is generated via a coupling mechanism that transmits tensile force.

The mechanical coupling mechanism can be designed as an articulated rod or tensioning means, depending on how the arrangement of the coupling mechanism on the upper part and on the foot part is configured. In a design as an articulated rod, it is possible that, up to a certain knee angle, the articulated rod permits a transmission of compressive force or also a transmission of tensile force, and, after the predetermined knee angle is reached, the articulated rod is buckled at the joint such that no appreciable transmission of force can take place any longer or a reversal of the direction of force takes place. The knee joint angle at which the articulated rod buckles is derived from the geometric relationships between the upper articulation point of the coupling mechanism and the lower articulation point and, if appropriate, a pretensioning of the joint. Starting from an initial position, the articulated rod can be buckled only in one direction, such that, before the predetermined knee joint angle is reached, a safe transmission of force is always possible and a reversal to the initial position can safely take place. The ankle joint can be pretensioned in a dorsiflexion direction in order to be able to effect a dorsiflexion in the absence of the force introduction via the coupling mechanism or the hydraulic system without reversal of the force direction.

To be able to make an adjustment to the wishes of the patient and to the physical circumstances presented by the latter, at least the first bearing point is designed to be adjustable, such that the distance of the first bearing point from the knee joint axis or the ankle joint axis is adjustable. In addition to the distance, the position in relation to the respective axis can also be adjustable, so as to be able to adjust the degree of displacement or plantar flexion of the foot part in accordance with the flexion of the knee. Depending on the lever ratio, a greater or lesser plantar flexion can be adjusted.

In a hydraulic force transmission mechanism, a control mechanism and if appropriate a switch valve can be provided in order to permit or interrupt a force transmission. The interruption of the enablement of the force transmission can take place on the basis of sensor values, an angle setting and/or a particular load situation, for example in accordance with the knee angle, the ankle joint angle or measured forces or moments. The control mechanism can be controlled either mechanically or electrically. In the case of a mechanical control, a control mechanism can be attached for example to the knee joint and can be designed, for example, as a control disk, a control cam or the like, such that a defined hydraulic reaction is initiated depending on the attained knee angle. A corresponding design can be provided for the ankle joint. After a defined angle has been reached, the force transmission can then be interrupted or a movement reversal per switch can take place in such a way that a dorsiflexion is initiated when a predetermined knee angle is reached. Also in the event of a movement reversal of the lower leg part in the swing phase, valve adjustment by switching in such a way that a dorsiflexion is effected in an extension movement of the knee joint. If sensors are used which detect certain loads, movements, angles or other parameters, the detected sensor values can be used to control the force transmission, i.e. to permit or interrupt a force transmission or transmit only some of the forces. The sensors are coupled to the sensor mechanism, which receives the sensor signals, processes them and, via an actuator, for example a valve, opens or closes in order to modify a flow of fluid.

A cylinder/piston unit can be arranged in each case on the upper part or the thigh part and on the shin part or the lower part or foot part, which cylinder/piston units are connected to each other by at least one hydraulic line. As a result of the movement of the knee, pressure is exerted on the upper hydraulic unit and is carried via a corresponding line and, if appropriate, a valve block to the lower hydraulic unit in order to actuate the foot part.

The cylinder/piston units are connectable to each other in parallel or crosswise via valves. It is likewise possible for an individual adjustment, including blocking of the cylinder/piston units, to be performed by the control mechanism in order to release or actuate the foot part as a function of the respective knee setting, direction of movement, speed of movement, acceleration of movement or gait situation.

A sensor mechanism can be provided for detecting the knee angle, the angle velocity or angle acceleration, which sensor mechanism is connected to a control mechanism for adjusting a valve or several valves, such that an electronically controlled valve switch is provided in order to control the hydraulic or mechanical transmission of force.

The force transmission mechanism can block a force transmission in the dorsiflexion direction, in order to ensure that a shift during the stance phase does not lead to unwanted flexion of the knee. Provision can be made that the maximum dorsiflexion position is variably adjustable, i.e. a dorsiflexion abutment is provided which is adjustable in order to be able to adapt to the respective user or the conditions of use. The dorsiflexion abutment can be designed as a mechanical abutment or can be realized by closing a valve.

A restoring device can be assigned to the foot part in order to effect a dorsiflexion of the foot part. For example, the restoring device can be designed as a spring or elastomer element which counteracts a plantar flexion. The ankle joint can be designed as an elastic joint in which an elastic element, for example an elastomer body, is arranged, wherein a restoring force is applied by the elastic joint to the foot part, such that the foot part is moved back to the initial position without the action for external forces.

In one embodiment, at least one damper, which counteracts a dorsiflexion, is present in the ankle joint, such that a restoring movement can be performed without overswing after a plantar flexion.

BRIEF DESCRIPTION OF THE DRAWINGS

Illustrative embodiments of the invention are explained in more detail below with reference to the attached figures, in which:

FIG. 14 shows a sectional view of a surface-side cylinder/piston unit in the dorsiflexion position;
FIG. 15 shows an embodiment according to FIG. 14 in the plantar flexion position.

DETAILED DESCRIPTION

Figure 1:
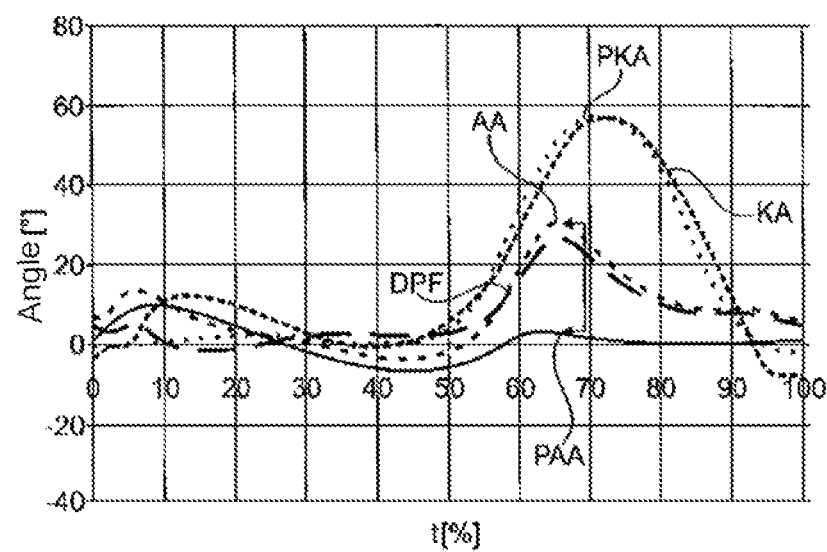
FIG. 1 shows ankle angle and knee angle profiles.

FIG. 1 shows different angles over time during a gait cycle. The natural knee angle KA and the natural ankle angle AA are shown by broken lines, the prosthetic knee angle PKA and the prosthetic ankle angle PAA are shown by solid lines over time during a step from heel strike to renewed heel strike. While the natural knee angle KA can be approximated very closely by a prosthetic device, as can be seen from the small differential angle and from an almost congruent profile of the knee angles KA and of the prosthetic knee angles PKA, the prosthetic ankle angle PAA deviates greatly from the natural ankle angle AA, the extent of the deviation being indicated by the differential angle ΔPF. The maximum deviation is present, in approximately two thirds of the gait cycle, shortly before toe-off when, in a natural gait phase, the maximum plantar flexion is ca. 30° starting from the initial position when standing, whereas the maximum plantar flexion in a prosthesis is approximately 2°, which is caused by the dynamics of the foot.

Figure 2:
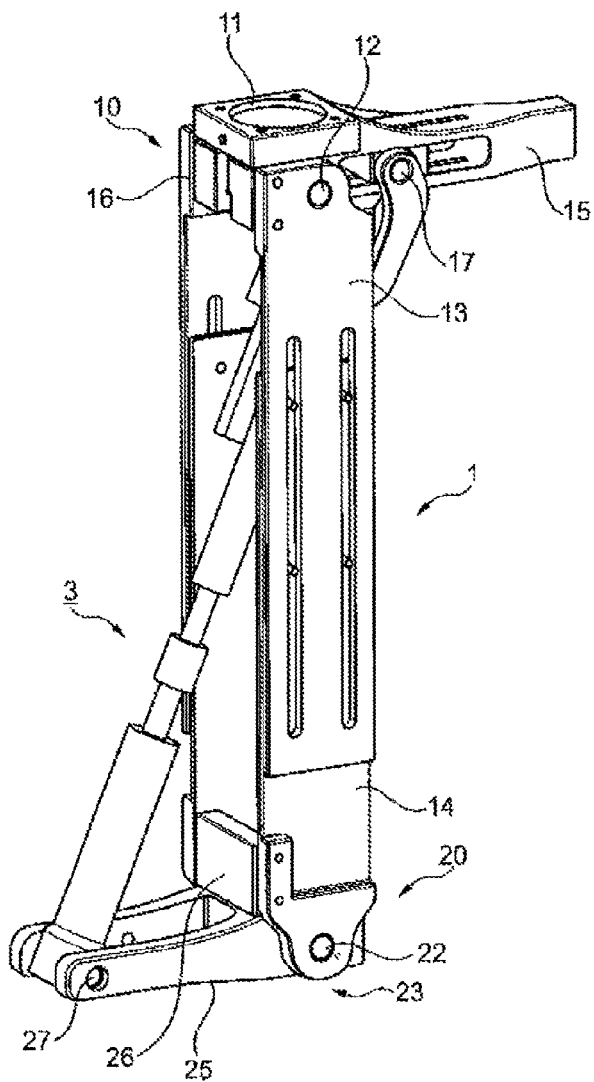
FIG. 2 shows a perspective view of a device.

To provide a gait pattern that is as natural as possible, a first embodiment of an orthopedic device 1 in the form of a lower leg prosthesis according to FIG. 2 is proposed, which has a knee joint 10 with a proximal upper part 11 and with a lower part 13 secured thereon pivotably about a knee axis 12. On the distal lower part 13, a shin part 14 is secured which provides a connection to the ankle joint 20 and is mounted on the foot part 23 so as to be pivotable about an ankle joint axis 22. In the illustrative embodiment shown, the foot part 23 is designed as a seat for an adjustment core for a prosthetic foot and has a jib 25 which, in the illustrative embodiment shown, is directed forward in the walking direction, i.e. has an anterior orientation. The lower part 13 and the shin part 14 have slotted guides, such that the two components are mounted movably on each other, so as to be able to make a length adjustment if this is desired or necessary. The lower part 13 is composed of two side plates, which are secured on shin parts 14 likewise designed as side plates, with the side plates lying congruently on each other. An abutment 16 for limiting the maximum extension angle is provided on the lower part 13, and an ankle abutment 26, which limits the maximum dorsiflexion of the foot part 23, is likewise provided on the shin part 14.

Arranged on the upper part 11, which is mounted so as to be pivotable clockwise about the knee axis 12, there is a jib 15 which faces rearward in the walking direction, i.e. has a posterior orientation, and in which an oblong hole guide is formed in which a distal articulation point 17 for a force transmission mechanism 3 is mounted. The articulation point 17 is arranged movably inside the oblong hole guide and is fixed there, by an orthopedic technician, in the correct position for the patient. The exact set-up of the force transmission mechanism 3, which in the depicted illustrative embodiment is designed as a mechanical coupling element in the form of an articulated rod, will be explained in more detail below.

The lower end of the coupling element is mounted in a distal articulation point 27 on the distal jib 25 in an articulated but immovable manner. By means of the arrangement of the articulation points 17, 27 posterior and anterior of a connection line between the knee axis 12 and the ankle joint axis 22, the clockwise rotation of the proximal articulation point 17 mounted eccentrically with respect to the knee axis 12 means that a flexion of the knee joint 10 leads to a movement of the coupling element and to a rotation of the distal jib 25 counterclockwise about the ankle joint axis 22, such that the foot part 23, with the prosthetic foot (not shown) secured thereon, is flexed in the plantar direction when the knee is flexed.

Figure 3:
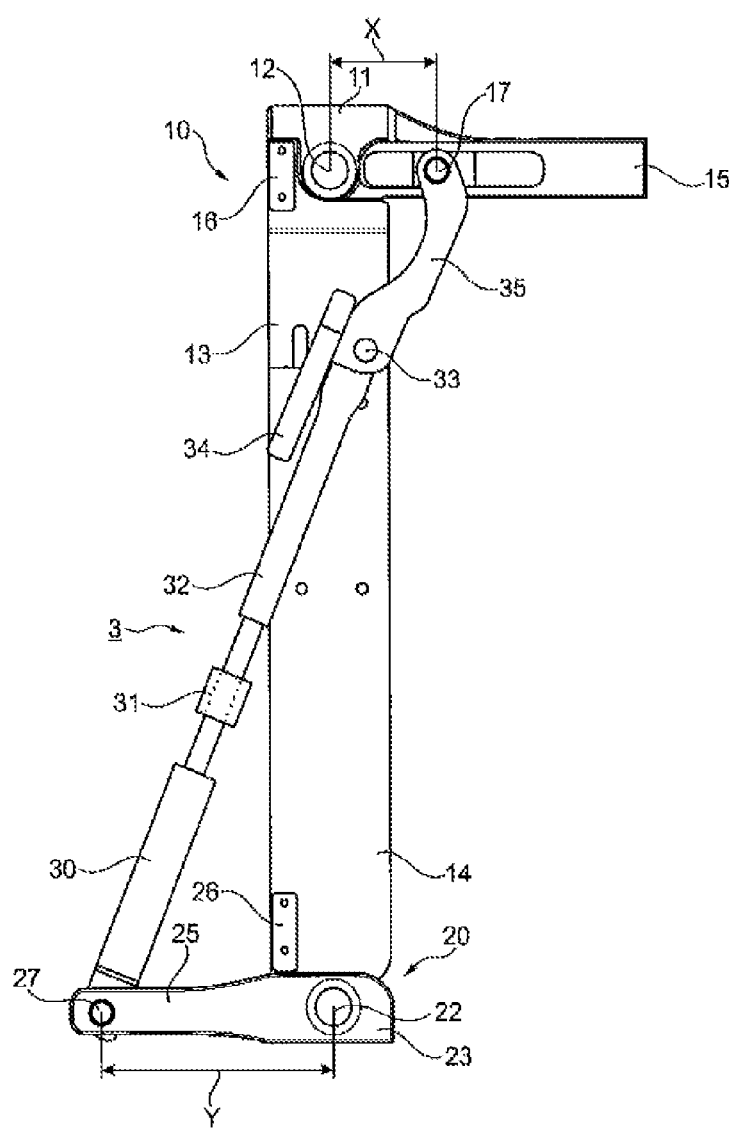
FIG. 3 shows a side view of the device according to FIG. 2 in an extended position.

FIG. 3, which is a sectional view from the side, shows the prosthesis 1 according to FIG. 2 in an initial position, which corresponds to standing. The knee joint 10 is located at the maximum extension, and the jib 25 of the ankle joint 20 is substantially at right angles to the longitudinal extent both of the shin part 14 and also of the lower part 13 and the connection line between the knee axis 12 and the ankle joint axis 22.

The oblong hole guide for the proximal articulation point 17 can be seen on the distal jib 15, likewise the proximal lever length X, which can be variably adjusted. The ankle lever length Y, which represents the distance between the distal articulation point 27 and the ankle joint axis 22, is indicated on the distal jib 25. The figure also shows clearly the mechanical force transmission mechanism 3 with a distal sleeve 30, which is mounted in an articulated manner on the ankle jib 25, a double screw 31 with opposite threads, and a proximal sleeve 32, which is mounted on a bracket 35 so as to be pivotable about a hinge axis 33. An abutment 34 formed on the bracket 35 prevents the proximal sleeve 32 from deflecting clockwise about the axis 33 beyond a predetermined angle.

Figure 3A:
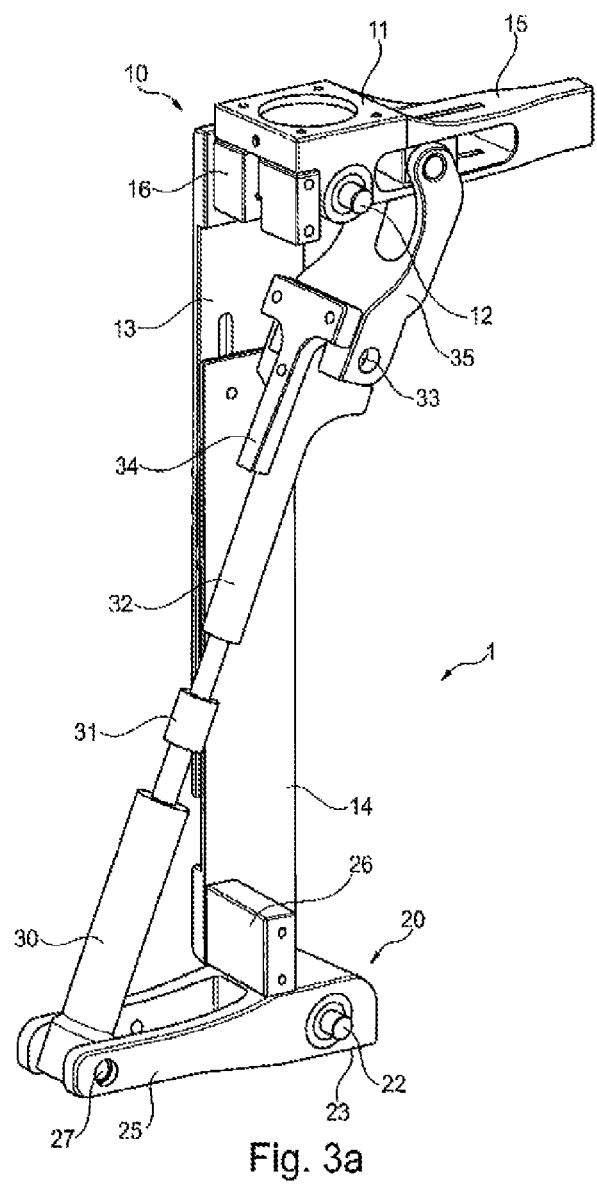
FIG. 3a shows a perspective view according to FIG. 3.

FIG. 3a shows the prosthesis 1 in a perspective view according to FIG. 3. It can be seen clearly from the perspective view that the ankle jib 25 is designed as a fork that is open on one side and that has two branches between which the distal sleeve 30 is mounted pivotably on the distal articulation point 27. Both the distal sleeve 30 and also the proximal sleeve 32 have an inner thread into which the double screw 31 is screwed. The proximal sleeve 32 is mounted about the hinge axis 33 on the bracket 35, which in turn is secured on the proximal jib 15. The upper part 10 is mounted via pins on the lower part 13 so as to articulate about the pivot axis 12, and the abutment 34 prevents the proximal sleeve 32 from pivoting clockwise about the hinge axis 33 beyond the fixed extent, which is defined by the abutment 34.

The mechanical dorsiflexion abutment 26, by means of which the maximum dorsiflexion of the foot part 23 is fixed, is secured on the shin part 14. The dorsiflexion abutment 26 is adjustable, such that the maximum dorsiflexion can be variably adjusted.

Figure 4:
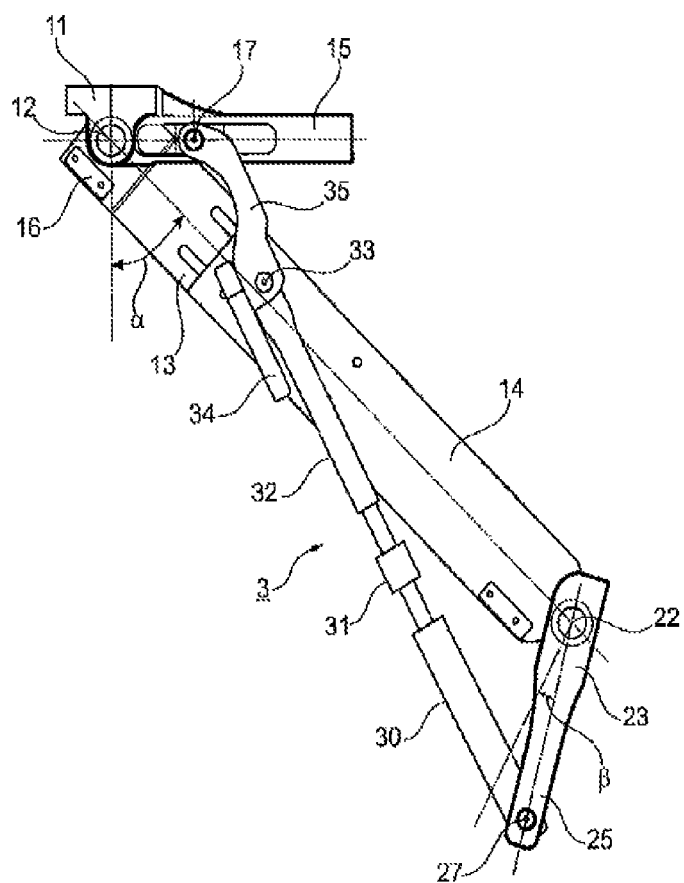
FIG. 4 shows a device according to FIG. 3 in a flexed position.

FIG. 4 shows the prosthesis 1 in a flexed state. Whereas the knee angle α was 0° in FIG. 3, a knee angle of approximately 50° is provided in FIG. 4. The plantar flexion angle β, which was 0° in the position according to FIG. 3, is ca. 25° in FIG. 4, which can be varied by the different lever lengths X, Y in the respective jibs 15, 25. If the lever length Y on the ankle jib 25 is also adjustable, the transmission ratio, in interaction with a length adjustment, can be performed easily via the double screw 31. The initial position, that is to say the plantar flexion angle β as a function of the knee angle α in the position according to FIG. 3, can be adjusted via the double screw 31 and the position of the proximal articulation point 17 inside the oblong hole guide. When the double screw 31 is unscrewed from the threads in the sleeves 30, 32, the force transmission mechanism 3 lengthens, such that, with a constant position of the articulation points 17, 27, the foot part 23 is flexed in the plantar direction and, conversely, with an opposite direction of rotation, a dorsiflexion is initiated.

FIG. 4 shows, for the illustrative embodiment, the maximum knee angle α up to which a compressive force can be transmitted to the distal jib 25, by the force transmission mechanism composed of the two sleeves 30, 32, the double screw 31 and the bracket 35, without the distal sleeve 32 pivoting about the axis 33. An abutment can be formed in the bracket 35; a further rotation of the bracket 35 relative to the jib 15 can likewise be prevented by other mechanisms, such that, with a further flexion in the knee joint 10, the distal end of the bracket 35 is shifted in the clockwise direction, such that buckling takes place in the force transmission mechanism 3, which leads to a shortening of the effective length between the two articulation points 17, 27. This leads to a reduction of the plantar flexion angle β, which can be supported by a pretensioning mechanism, for example in the form of a spring. As a result of the reduction of the plantar flexion angle β, the effective leg length is reduced by the tip of the prosthetic foot (not shown) being moved in the dorsiflexion direction and lifted, such that an easier swing through can take place in the swing phase if an extension movement is performed in the knee joint 10.

In principle, it is also possible for the jibs 15, 25 to be oriented in the respectively reverse direction, i.e. the proximal jib 15 in the anterior direction and the distal jib 25 in the posterior direction, in which case the force transmission mechanism 3 works mainly by transmitting tensile force when the knee joint 10 is flexed.

Figure 5:
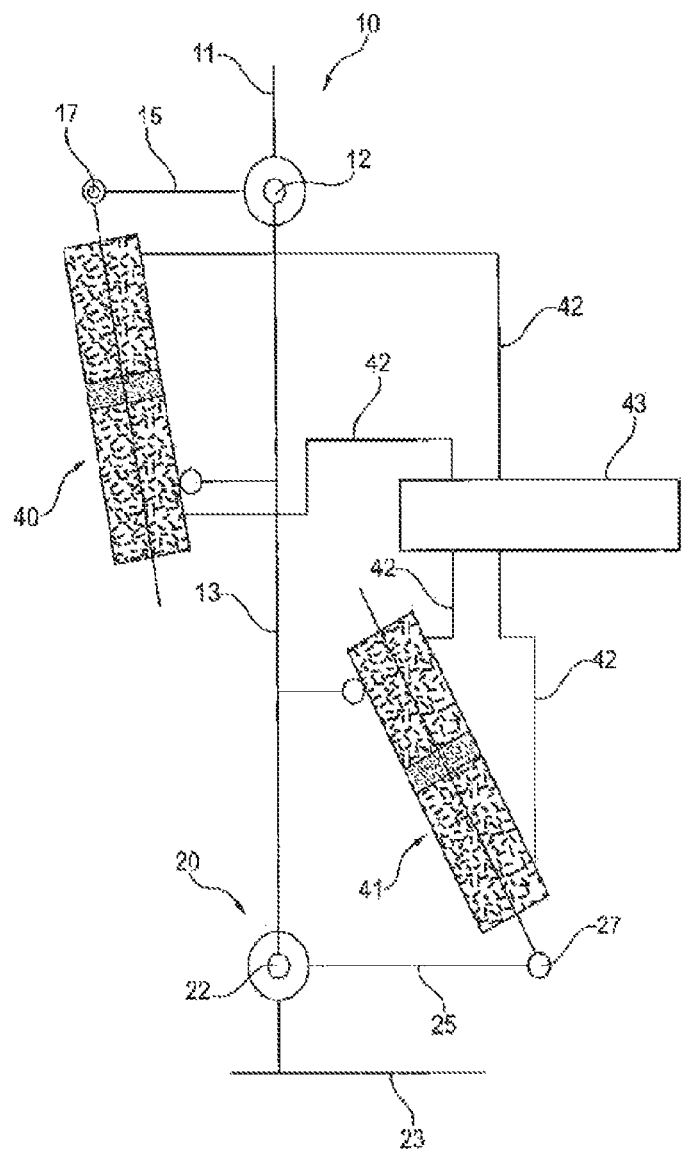
FIG. 5 shows a block diagram of a hydraulic force transmission.

FIG. 5 shows a basic set-up of a hydraulic force transmission mechanism 3. Here too, jibs 15, 25 are provided on the knee joint 10 and on the ankle joint 20. In a very simple design of the knee joint 10, the lower part 13 can at the same time form the connection between the knee joint 10 and the ankle joint 20. Generally, the knee joint 10 is designed as a separate component and has an upper part 11 and a lower part 13, on which it is possible to secure, by securing means, a shin tube or shin part 14, which in turn is fixed on securing means of the ankle joint 20 of a prosthetic foot. In the illustrative embodiment shown, a first hydraulic cylinder/piston unit 40 is mounted on the proximal articulation point 17 and on the lower part 13. By way of hydraulic lines 42 that open into a valve block 43, a distal cylinder/piston unit 41 is connected to the proximal cylinder/piston unit 40 in terms of flow. The distal piston/cylinder unit 41 is optionally mounted on the lower part 13 or on a shin part and also on the jib 25 at the distal articulation point 27. When the knee joint 10 is flexed, the piston inside the proximal piston/cylinder unit 40 moves downward, hydraulic fluid is conveyed through the line 42 into the valve block 43 and from there into the upper chamber of the distal piston/cylinder unit 41, such that a plantar flexion of the foot part 23 about the ankle joint axis 22 is effected.

In the illustrative embodiment shown, the two hydraulic units 40, 41 are designed as two unidirectional cylinders, which are of the same configuration in terms of volumes and diameters. An individual transmission can be achieved by different levers on the knee joint 10 and on the ankle joint 20.

A plurality of different valves can be provided in the valve block 43 so as to connect all the cylinder volumes to each other in any desired manner, in order to be able to set different plantar flexion angles β at desired knee angle adjustments. Proportional valves may be present inside the valve block 43, by means of which it is possible to perform throttling, such that different hydraulic resistances can be made available. By different connection of the individual cylinders, it is possible, depending on the type of movement and the phase of movement, to achieve a desired adjustment of the foot part 23 as a function of the knee angle α.

Figure 6:
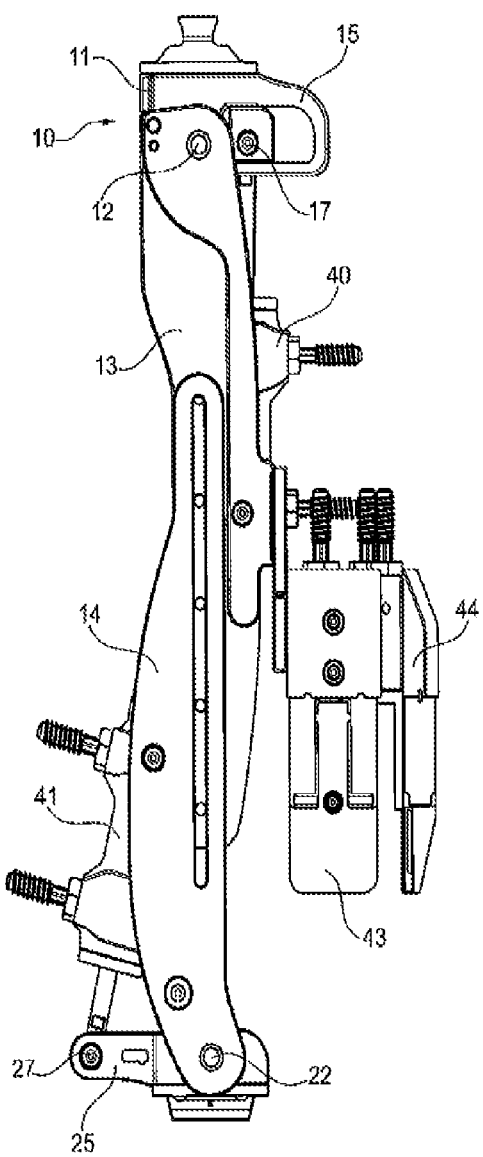
FIG. 6 shows a schematic view of a prosthesis device with a hydraulic unit.

FIG. 6 shows a schematic side view of a prosthetic device with hydraulic force transmission. Similarly to the illustrative embodiment according to FIG. 2, an oblong hole guide is provided in the proximal jib 15, and the upper articulation point 17 of the proximal piston/cylinder unit 40 is mounted in said oblong hole guide. The lever length X, and therefore the mechanical gearing, can be adjusted via a fixing mechanism. A pyramid adapter is secured on the upper part 11 of the knee joint 10, while vertically adjustable shin parts 14 are mounted on the lower part 13 of the knee joint 10 with the side plates, between which the distal piston/cylinder unit 41 is arranged. The lower articulation point 27 is rotatable but mounted non-displaceably on the distal jib 25 on which sensors, for example in the form of strain gauges, can be arranged in order to detect the load. The valve block 43 is provided with a control device 44 in which switching electronics are accommodated, such that the valves arranged inside the valve block 43 can be used for different coupling of the cylinders in the cylinder/piston units 40, 41 individually and after evaluation of sensor data.

Figure 7:
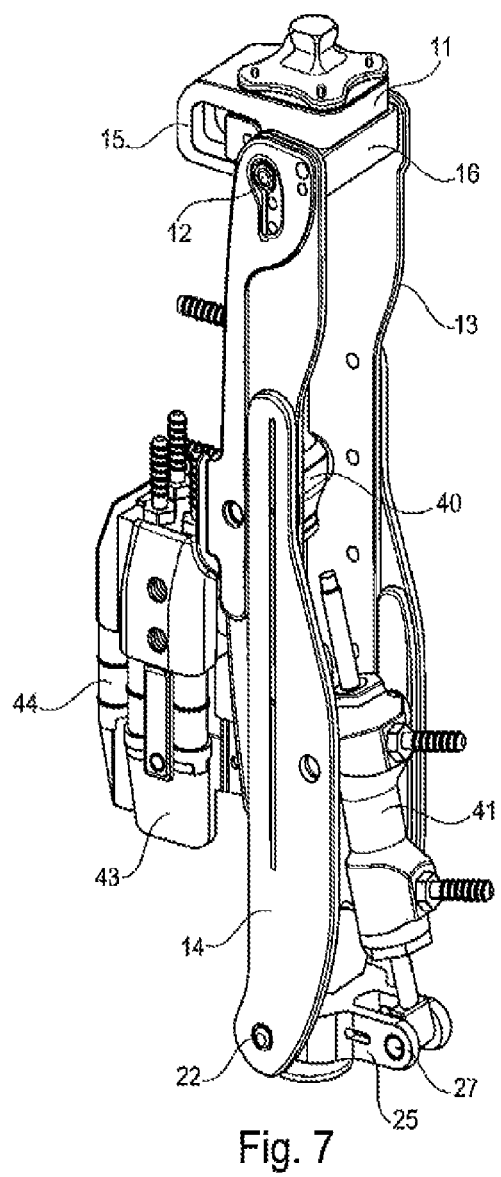
FIG. 7 shows a perspective view of the embodiment according to FIG. 6.

FIG. 7 shows a perspective view of the illustrative embodiment according to FIG. 6, from which view it can be seen that the hydraulic cylinder units 40, 41 are arranged between the shin parts 14 and lower parts 13 designed as side plates. The valve block 43 can likewise be arranged between the side plates.

Figure 8:
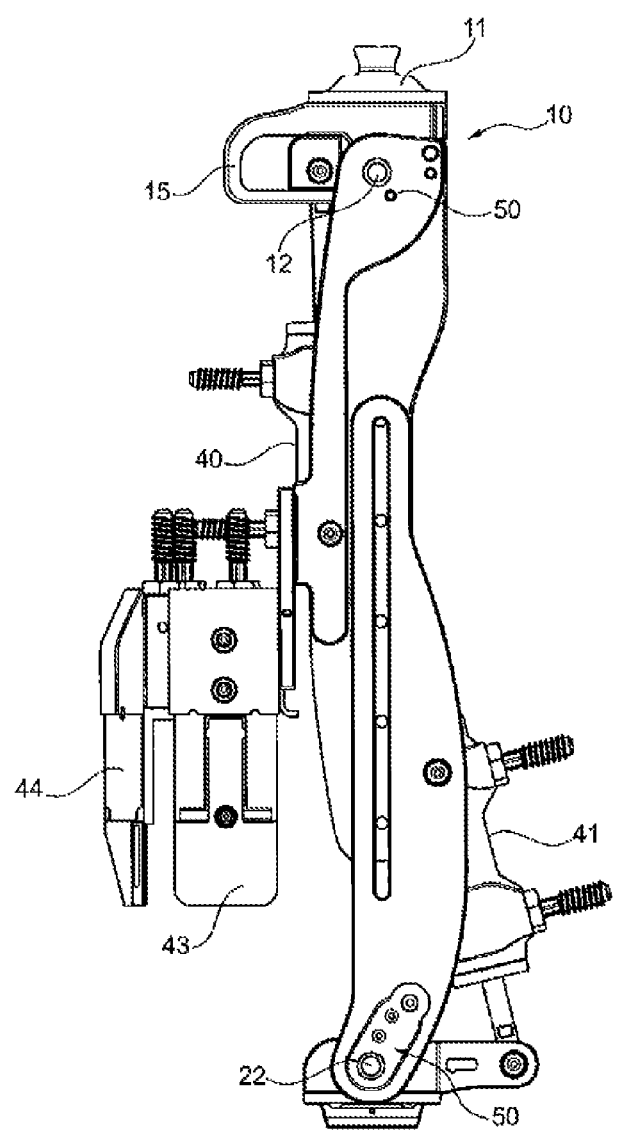
FIG. 8 shows a mirror-image view of the embodiment according to FIG. 6.

FIG. 8 shows a variant of the invention in which angle sensors 50 both in the knee joint 10 and also in the ankle joint 20 are coupled to the control unit 44, such that, as a function of the knee angle α and the plantar flexion angle β, the valves inside the valve block 43 can be switched in an angle-dependent manner. It is likewise possible to provide other sensors, for example position sensors or force or moment sensors, in order to determine the spatial position, forces or moments and use these to control the valves.

Figure 8A:
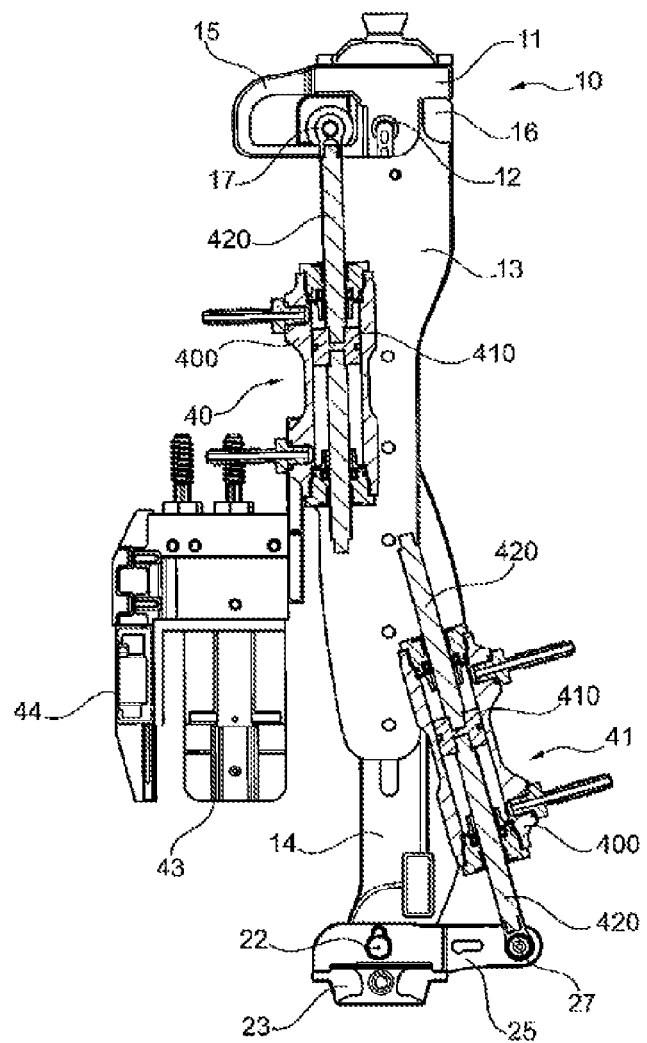
FIG. 8a shows a sectional view of FIG. 8.

FIG. 8a shows a sectional view of FIG. 8. In the upper part 11, mounted on the lower part 13 in an articulated manner about the pivot axis 12, and in the extension abutment 16, the proximal jib 15 in FIG. 8a can be seen with the oblong hole guide for the proximal articulation point 17. A piston rod 420 of the proximal cylinder/piston unit 40 is secured on the proximal articulation point 17. A piston 410 is secured on the piston rod 420 and is guided in a housing 400 of the piston/cylinder unit 40. In the completely extended position of the knee joint 10 illustrated, the piston 410 of the proximal cylinder/piston unit 40 is located on the proximal abutment. By way of hydraulic lines (not shown), which open into the valve block 43 and are opened, completely closed or partially closed by the control unit 44 via corresponding valves, the hydraulic fluid is conveyed from the distal cylinder chamber to the distal cylinder/piston unit 41 during a flexion movement. Starting from the neutral position shown, hydraulic fluid is conveyed into the proximal cylinder chamber of the distal cylinder/piston unit 41 when the knee joint 10 is flexed, such that the distal piston rod 420 is shifted in the direction of the distal bearing point 27, such that a plantar flexion takes place about the ankle joint axis 22.

Figure 9:
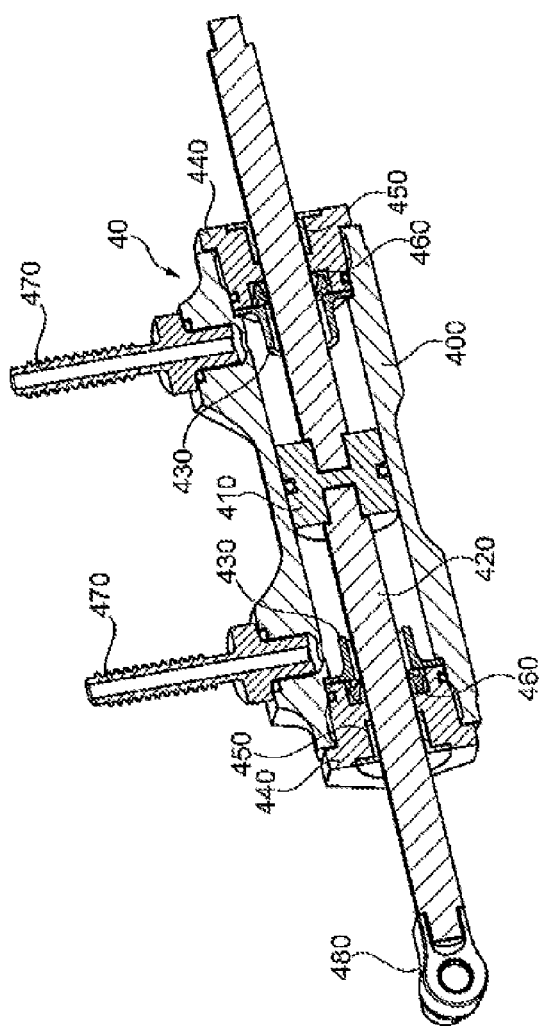
FIG. 9 shows a sectional view of a cylinder/piston unit.
Figure 10:
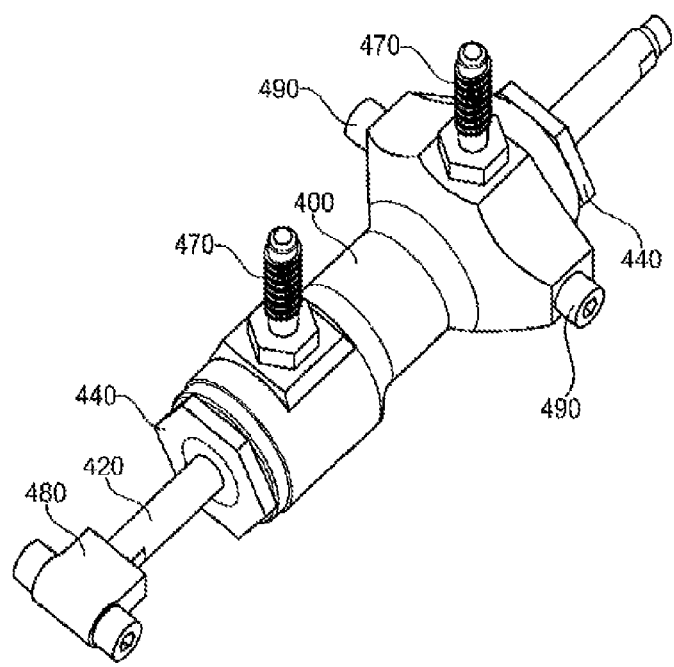
FIG. 10 shows a perspective overall view of a cylinder/piston unit.

FIG. 9 shows a detailed view of a piston/cylinder unit with a housing 400, in which a piston 410 is secured on a piston rod 420. Two end abutments 430 limit the volume bounded by the housing 400. The cylinders formed by the housing 400 are closed by lids 440. Slide bearings 450 and wipers 460 are integrated in the lids 440. On each end of the two cylinders that are separated by the piston 410, hose attachments 470 are provided, which are connected to hydraulic lines 42 (not shown). A bearing bolt 480 is arranged on the piston rod 420, which bearing bolt 480 can be arranged in one of the articulation points 17, 27 of the jibs 15, 25. The bearing bolt 480 can be provided as a joint head with two axial pins for bearing on the jibs 15, 25, while a second bearing point is shown in the perspective view according to FIG. 10. The axial pins 490 in the housing 400 serve for bearing in the side plates either of the lower part 13 or of the shin part 14.

Figure 11:
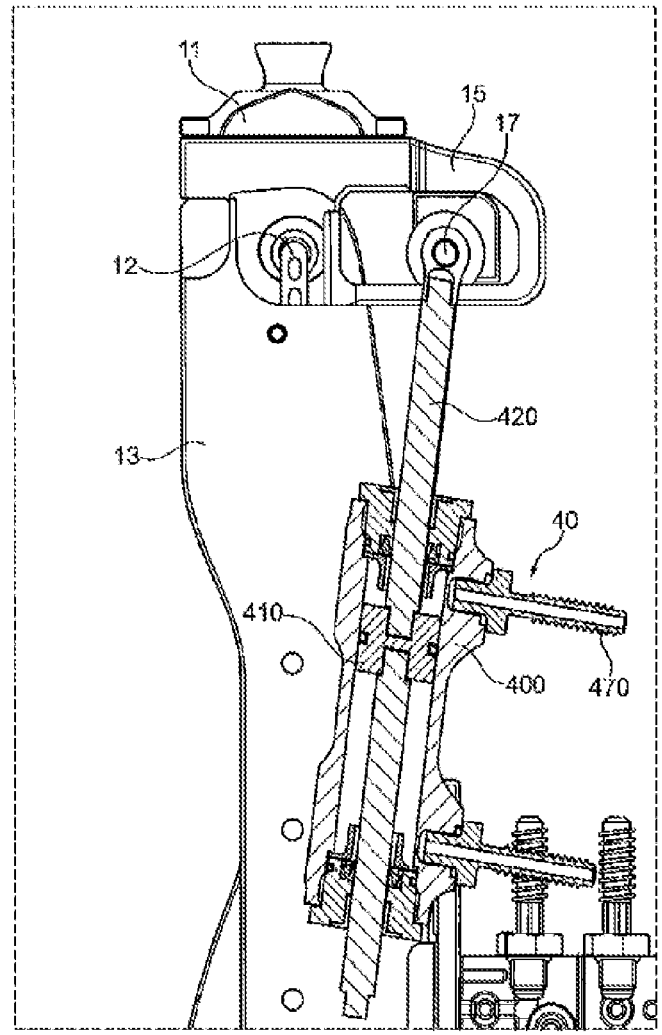
FIG. 11 shows a cross-sectional view of an installed cylinder/piston unit in the extended state.
Figure 12:
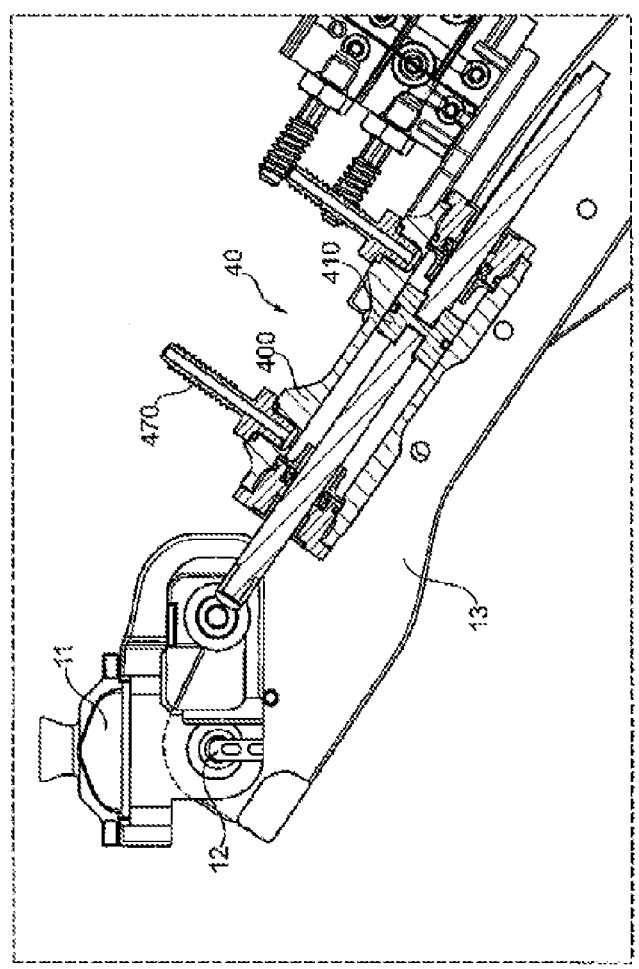
FIG. 12 shows a device according to FIG. 11 with a flexion angle of 60°.
Figure 13:
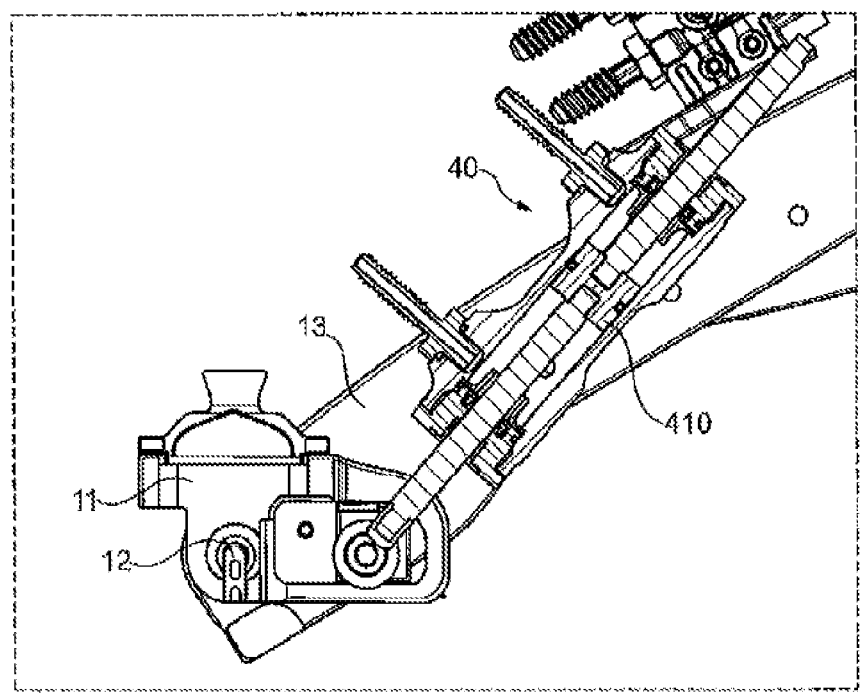
FIG. 13 shows a device according to FIG. 11 with a flexion angle of 120°.

FIGS. 11 to 13 show a cross-sectional view of the proximal piston/cylinder unit 40 in different knee angle positions. In the position shown in FIG. 11, the knee angle is 0°, and the piston 410 inside the housing 400 is then located in the maximum position at the proximal end abutment. All the hydraulic fluid has been pressed out of the proximal cylinder, and the volume of the distal cylinder is maximal.

FIG. 12 shows a knee angle position with a knee angle α of 60°. The piston 410 is located past the middle of the housing 400, such that the proximal cylinder has a greater volume than the distal cylinder. By the flexion of the knee joint, the piston 410 has been moved downward inside the cylinder, and hydraulic fluid from the lower cylinder has been conveyed through the valves to the distal piston/cylinder unit 41 (not shown).

FIG. 13 shows a position of the knee joint with a knee angle α of 120°, as is adopted when kneeling down or squatting. The position of the piston 410 corresponds to that of FIG. 12, but the piston 410 has already reached the distal end abutment at a position of a knee angle α of 90°. The reverse movement of the piston 410 when passing through the knee angle of 90° can either lead to the reverse movement in the control of the ankle joint 20 or can be compensated by a switching of the valves.

FIG. 14 shows the arrangement of a piston/cylinder unit 41 on the ankle joint 20 with a dorsiflexion in which the piston 410 is positioned close to the proximal end abutment 430. FIG. 15 shows an ankle joint 20 at maximum flexion, for example at a knee angle α of 90°.

Figure 16:
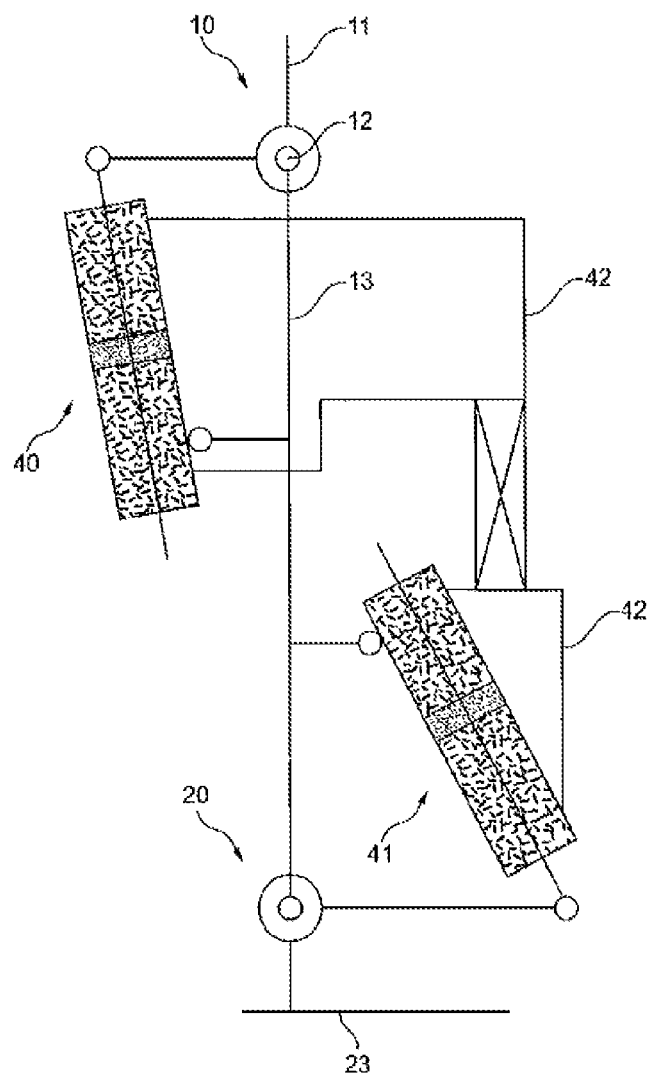
FIG. 16 shows a schematic view of different switching possibilities.

FIG. 16 shows a schematic view of different switching possibilities. The hose attachments 470 can be switched in parallel, and it is likewise possible that the hose attachments 470 of the distal piston/cylinder unit 41 are switched crosswise with the hose attachments 470 of the proximal piston/cylinder unit 40. It is likewise possible that the piston/cylinder units 40, 41 are switched independently of each other, such that no functional connection is present between the units. The knee joint 10 and the ankle joint 20 are therefore freely movable independently of each other; if appropriate, the damping in the knee joint 10 and/or the ankle joint 20 can be adjusted via a throttle valve. If the proximal piston/cylinder unit 40 is switched free while the distal piston/cylinder unit is blocked, the knee joint 10 is freely movable and the ankle joint 20 is rigid, and, when both piston/cylinder units 40, 41 are blocked, both joints are rigid.

By virtue of the controlled flexion and extension in the ankle joint 20 as a function of the knee angle α and a coupling of the plantar flexion as a function of the knee flexion, it is possible to use the kinetic energy of the knee for the ankle movement. This achieves a lengthening of the effective leg length in the knee flexion at the end of the stance phase, and in this way the duration of the ground contact is lengthened, as a result of which the vertical movement of the center of gravity of the body during walking is minimized. This results in an approximation to the natural gait pattern. By virtue of the dorsiflexion in the swing phase, it is possible again to shorten the effective leg length in order to minimize the likelihood of stumbling. On account of the direct conversion of the mechanical energy with minimal loss of performance, it is possible to attain a high level of energy efficiency with a relatively low weight when compared to known orthotic devices, in particular prostheses with motorized adjustment mechanisms.

Figure 17:
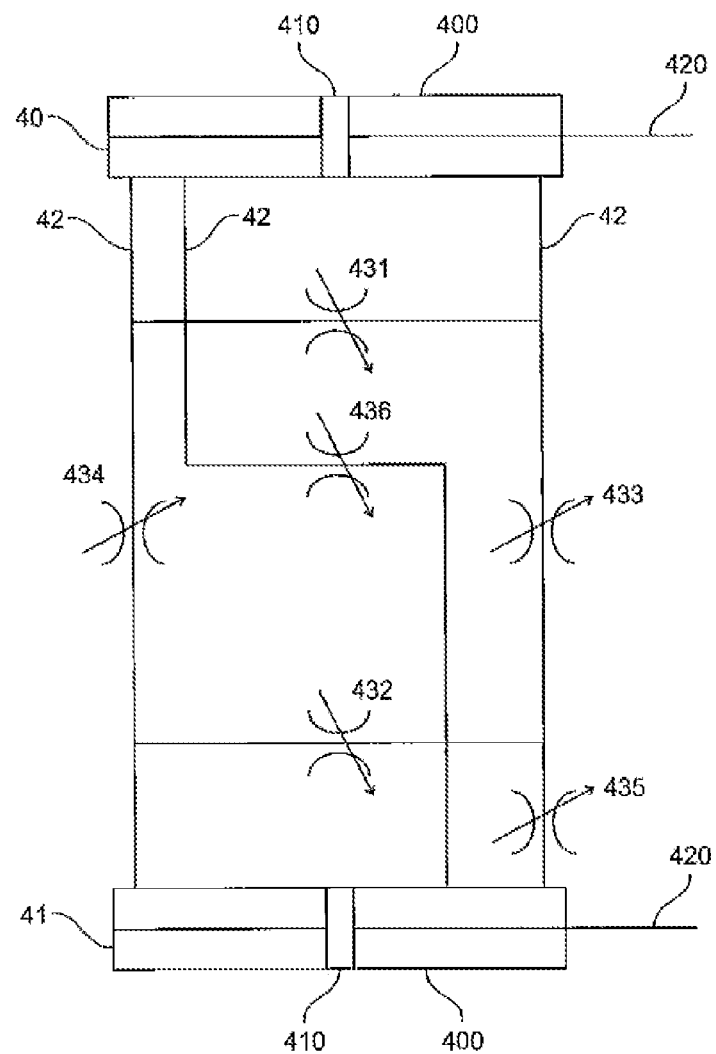
FIG. 17 shows a schematic view of a valve arrangement.

In FIG. 17, the two cylinder/piston units 40, 41 assigned respectively to the knee joint and to the ankle joint are each shown schematically in the neutral position. The piston rod 420 protruding in each case from the housing 400 is secured, for example, on the respective jibs 15, 25 in order to permit a force transmission, while the other end of the piston/cylinder unit is mounted on the lower part or shin part.

The hydraulic lines 42 connect the cylinder chambers to each other in parallel, the hydraulic lines 42 are connected to each other by transverse lines, and a diagonal line connects a cylinder chamber facing away from the piston rods 420 to a cylinder chamber of the distal cylinder/piston unit 41 facing toward the piston rod 420.

At least one valve 431, 432, 433, 434, 435, 436 is arranged in each of the hydraulic lines 42 in order to be able to perform different switching procedures. For example, if the valves 433, 434, 435 are opened and the other valves 431, 432, 436 are closed, a parallel switching is obtained, which has the effect that a displacement of the upper piston 410 to the left leads to a displacement of the lower piston 410 to the right. In order to generate an opposite movement, the cylinder/piston units 40, 42 have to be switched crosswise, for which purpose the valves 431, 434 and 435 are closed while the valves 432, 433 and 436 are open.

When the valves 433, 434 and 436 are closed, this leads to a decoupling of the proximal piston/cylinder unit 40 from the distal cylinder/piston unit 41. By partial closure of the opened valves 431, 432 and 435, it is possible to adapt the resistance to displacement.

If only the upper valve 431 is opened, the ankle joint remains rigid, whereas the knee joint can be flexed, the resistance to the flexion arising from the hydraulic resistance of the opened valve 431. A rigid knee joint and movable ankle joint is possible if the valves 432, 435 are opened and the other valves remain closed.

Figure 18:
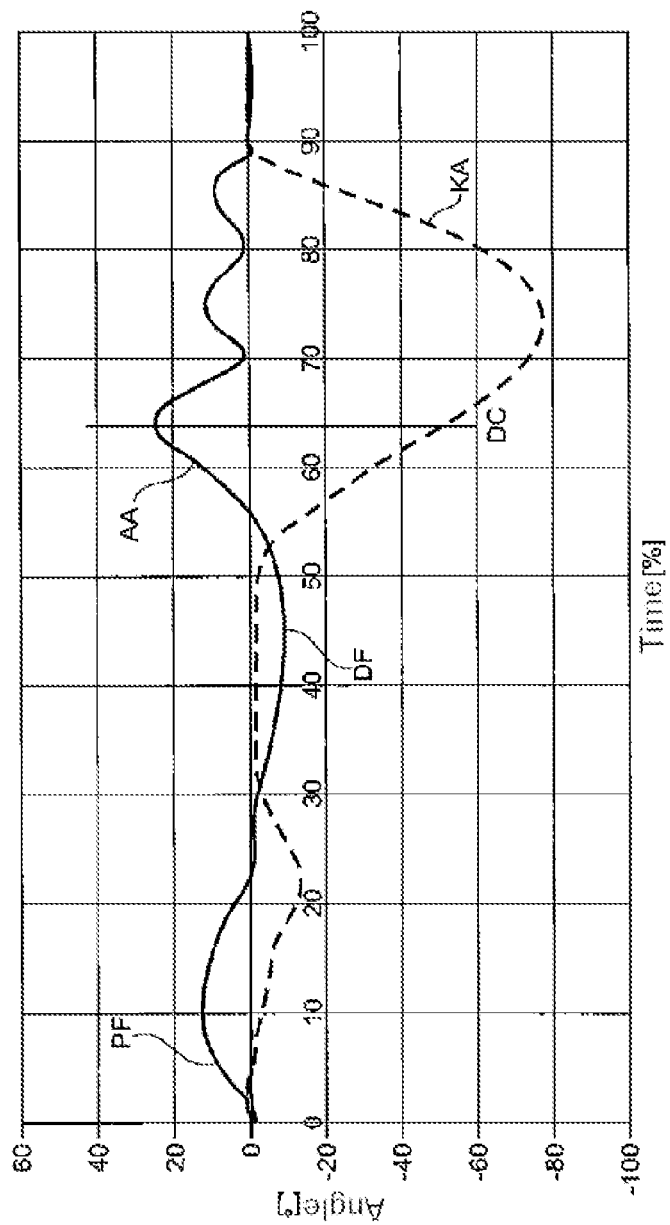
FIG. 18 shows angles of the knee and of the ankle joint over time.

FIG. 18 shows the profile of the knee angle KA and of the ankle angle AA in a prosthetic knee joint with a coupling device according to the invention during a gait cycle. After the heel has been set down, the so-called heel strike, a plantar flexion PF of the ankle joint takes place counter to a spring force for example, which holds the ankle joint in the initial position. The plantar flexion after the heel strike is effected by the transmission of forces from the knee flexion by way of the force transmission mechanism and superposes the force of the restoring spring acting in the direction of a dorsiflexion which, in the further profile, after approximately a quarter of the step duration, leads to a cancelling of the forces acting in opposite directions. The ankle joint angle is then 0° again. In the knee joint there is an initial stance phase flexion with simultaneous reduction of the ankle joint angle after reaching an initial local maximum at ca. 10% of the step duration. After the maximum extension of the knee joint is reached, the force introduction point migrates in front of the ankle joint after approximately one third of the step duration, as a result of which there is a dorsiflexion DF. After approximately half of the step duration, the knee angle KA increases, while at the same time a plantar flexion is initiated which, with flexion of the knee, conveys the arising forces to the ankle joint. After approximately two thirds of the step duration, a decoupling DC of the ankle joint from the knee joint takes place, such that the knee joint can swing freely rearward, while the ankle joint is moved back to the initial position after reaching the maximum plantar flexion. On account of a damper not present, this return movement takes place in the form of an attenuating oscillation.

Figure 19:
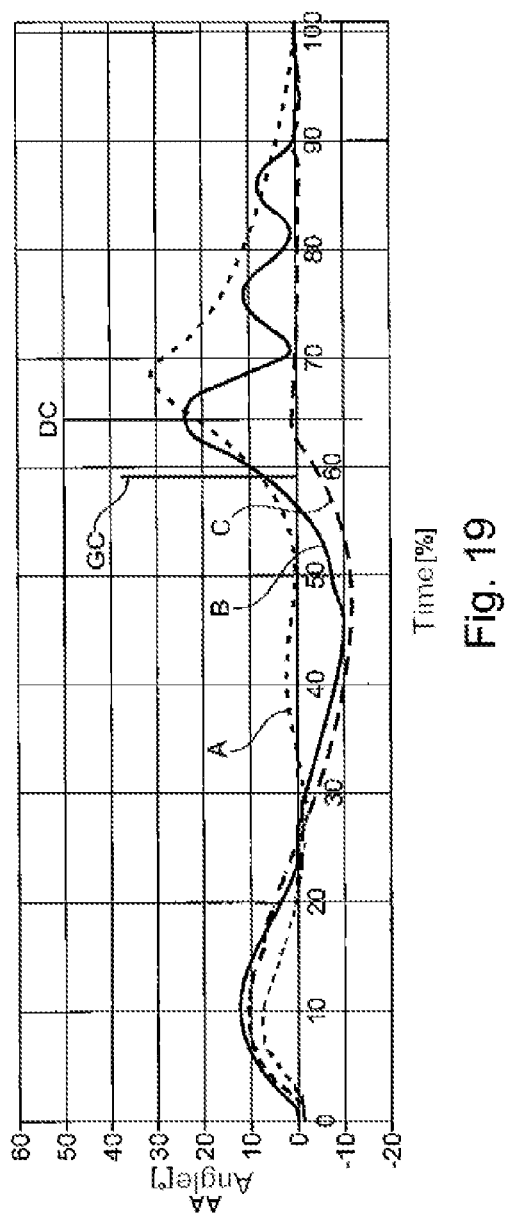
FIG. 19 shows superposed angle profiles of the ankle joint over time.

FIG. 19 shows different profiles of the ankle joint angle during the course of a step, wherein the curves A and B show angle profiles that are obtained with a device according to the invention, and curve C shows the profile of a conventional ankle joint. At the end of the ground contact GC, i.e. at the end of the terminal stance phase, the curves A and B reach a plantar flexion angle of between 8° and 10°, whereas a conventional ankle joint has a dorsiflexion of ca. 8°. After the decoupling DC of the force transmission mechanism from the ankle joint, a relatively quick dorsiflexion takes place on the curve B, since no damping mechanism is present there, the curve A provides damping, and in the curve C, after the end of the ground contact, the initial state is reached very quickly again.

The invention claimed is:

1. An orthopedic device for the orthotic or prosthetic provision of a patient, comprising:
   a knee joint, the knee joint having a proximal upper part and a distal lower part arranged pivotably thereon;
   an ankle joint;
   a pivotable foot part, which can be secured distally on the ankle joint;
   a shin part arranged between the ankle joint and the knee joint;
   wherein the upper part of the knee joint, or a thigh part that is secured thereon and can be fastened to the patient's body, is coupled to the foot part via a force transmission mechanism, which causes a plantar flexion of the foot part when the knee joint is flexed, the force transmission mechanism comprising a hydraulic system, the hydraulic system comprising:
   a first unit comprising a first cylinder and a first piston, the first unit being arranged on the upper part or the thigh part, the first piston dividing the first cylinder into a first hydraulic chamber and a second hydraulic chamber;
   a second unit comprising a second cylinder and a second piston, the second unit being arranged on the shin part or the foot part, the second piston dividing the second cylinder into a third hydraulic chamber and a fourth hydraulic chamber;
   at least one hydraulic line fluidly connecting the first and second units.

2. The orthopedic device as claimed in claim 1, wherein the force transmission mechanism further comprises a mechanical coupling mechanism that transmits at least one of tensile force and compressive force.

3. The orthopedic device as claimed in claim 2, wherein the mechanical coupling mechanism is mounted on a first bearing point protruding dorsally or ventrally with respect to a knee axis and is mounted on a second bearing point ventrally or dorsally with respect to an ankle joint axis, wherein the first and second bearing points lie on different sides of a connection line between the knee axis and the ankle joint axis.

4. The orthopedic device as claimed in claim 2, wherein the mechanical coupling mechanism is designed as an articulated rod or tensioning member.

5. The orthopedic device as claimed in claim 3, wherein at least the first bearing point is designed to be adjustable.

6. The orthopedic device as claimed in claim 2, wherein the force transmission mechanism has a control mechanism in order to permit or interrupt a force transmission.

7. The orthopedic device as claimed in claim 6, wherein the control mechanism is coupled to at least one sensor in order to control a force transmission in accordance with sensor values.

8. The orthopedic device as claimed in claim 1, wherein the cylinder/piston units are connectable to each other in parallel or crosswise via valves or individually adjustable.

9. The orthopedic device as claimed in claim 8, wherein a sensor mechanism is provided for detecting at least one of a knee angle ($\alpha$) and a plantar flexion angle ($\beta$), and is connected to a control mechanism for adjusting the valves.

10. The orthopedic device as claimed in claim 1, wherein the force transmission mechanism blocks a force transmission in the dorsiflexion direction.

11. The orthopedic device as claimed in claim 1, wherein a maximum dorsiflexion position of the foot part is designed to be variably adjustable.

12. The orthopedic device as claimed in claim 1, wherein a restoring device is assigned to the foot part in order to effect a dorsiflexion of the foot part.

13. The orthopedic device as claimed in claim 1, wherein the ankle joint is designed as an elastic joint and exerts a restoring force in the event of an excursion from a starting position.

14. The orthopedic device as claimed in claim 1, wherein at least one damper, which counteracts a dorsiflexion, is present in the ankle joint.

15. An orthopedic device, comprising:
a knee joint, comprising:
    a proximal upper part configured to be fastened to a patient;
    a distal lower part pivotally connected to the proximal upper part;
an ankle joint;
a foot part pivotally connected to the ankle joint;
a shin part positioned between the ankle joint and the knee joint;
a force transmission mechanism coupled to the foot part and operable to provide a plantar flexion of the foot part when the knee joint is flexed, the force transmission mechanism comprising a hydraulic system, the hydraulic system comprising:
    a first unit comprising a first cylinder and a first piston, the first unit being arranged on the upper part or a thigh part, the first piston dividing the first cylinder into a first hydraulic chamber and a second hydraulic chamber;
    a second unit comprising a second cylinder and a second piston, the second unit being arranged on the shin part or the foot part, the second piston dividing the second cylinder into a third hydraulic chamber and a fourth hydraulic chamber;
    at least one hydraulic line fluidly connecting the first and second units.

16. The orthopedic device as claimed in claim 15, wherein the force transmission mechanism further comprises a mechanical coupling mechanism that transmits at least one of tensile force and compressive force.

17. The orthopedic device as claimed in claim 16, wherein the mechanical coupling mechanism is mounted on a first bearing point protruding dorsally or ventrally with respect to a knee axis of the knee joint and is mounted on a second bearing point ventrally or dorsally with respect to an ankle joint axis of the ankle joint, wherein the first and second bearing points lie on different sides of a connection line extending between the knee axis and the ankle joint axis.

18. The orthopedic device as claimed in claim 16, wherein the mechanical coupling mechanism is designed as an articulated rod or tensioning member.

19. The orthopedic device as claimed in claim 17, wherein at least the first bearing point is adjustable.

* * * * *